United States Patent [19]

Arnold, Jr.

[11] Patent Number: 5,434,047
[45] Date of Patent: Jul. 18, 1995

[54] ASSAY FOR POLYNUCLEOTIDES EMPLOYING OLIGONUCLEOTIDES TO ELIMINATE UNDESIREABLE CROSS REACTIONS

[75] Inventor: Lyle J. Arnold, Jr., San Diego, Calif.

[73] Assignee: Gen-Probe Incorporated, San Diego, Calif.

[21] Appl. No.: 42,855

[22] Filed: Mar. 31, 1993

Related U.S. Application Data

[63] Continuation of Ser. No. 554,088, Jul. 17, 1990, abandoned, which is a continuation of Ser. No. 80,331, Jul. 31, 1987, abandoned.

[51] Int. Cl.$^6$ .................... C12Q 1/68; C07H 21/04
[52] U.S. Cl. ........................................ 435/6; 935/77; 935/78; 536/24.3
[58] Field of Search ................. 435/6; 935/77, 78; 536/24.3

[56] References Cited

U.S. PATENT DOCUMENTS

| | | | |
|---|---|---|---|
| 4,683,194 | 7/1987 | Saiki et al. | 435/6 |
| 4,755,458 | 7/1988 | Rabbani et al. | 435/5 |
| 4,766,062 | 8/1988 | Diamond et al. | 435/6 |

FOREIGN PATENT DOCUMENTS

| | | | |
|---|---|---|---|
| 82305489.5 | 10/1982 | European Pat. Off. | |
| 0097373 | 4/1984 | European Pat. Off. | 435/6 |
| 0164054 | 5/1984 | European Pat. Off. | |
| 0164054 | 5/1985 | European Pat. Off. | |

(List continued on next page.)

OTHER PUBLICATIONS

Kanter et al Analytical Biochemistry 97:77-84 (1979).
Wells et al Methods in Enzymology 65: 327-46 (1980).
Alonso et al Exp Cell Res 85 pp. 383-390 (1974).
Wallace Current Communications in Mol Biol: DNA Probes (1986) Cold Spring Harbor Laboratory; CSHL, N.Y.
Nozari et al Gene 43 pp. 23-28 (1986).
Maniatis et al, Molecular Cloning pp. 326-327 (1982) Cold Spring Harbor Laboratory; CSHL, NY.
Ludwig et al Virology 49 pp. 95-101 (1972).
Wallace et al Nucl Acids Res 9 pp. 879-894 (1981).
Hames et al. Nucleic Acid Hybridyzation: A Practical Approach pp. 3-4, 105-107, 122-123 (1985) IRL Press Limited Wash D.C.
Thein et al. Human Genetic Diseases: A Practical Approach pp. 33-49 (1987) IRL Press Limited Wash D.C.
Mamitis et al Molecular Cloning (1982) Cold Spring Harbor Laboratory Cold Spring Harbor N.Y. p. 387.
Shimizu et al., Clinical Chemistry, vol. 28, No. 3, 1982.
Weintraub, et al., Clinica Chimica Acta, vol. 48, No. 1, pp. 1-116.
Uotila et al., Journal of Immunological Methods, 42 (1981) 11-15 Elsevier/North Biomedical Press.
Katus et al., Moleculare Immunology, vol. 19, No. 3, pp. 451-455, 1982 Great Britain.
Conner et al., Proc. Natl. Acad. Sci 80:278 (1983).

(List continued on next page.)

Primary Examiner—Margaret Parr
Assistant Examiner—Carla Myers
Attorney, Agent, or Firm—Lyon & Lyon

[57] ABSTRACT

In an assay for a target nucleotide sequence employing hybridization with a target probe nucleotide sequence, cross reaction between the target probe and a non-target nucleotide sequence, capable of hybridizing with the target probe, is prevented or diminished by introducing, at some point during the hybridization, a non-target probe which hybridizes preferentially with the non-target nucleotide sequence. The melting temperature for the non-target probe/non-target nucleotide sequence hybrid is preferably greater than that of the target probe/non-target sequence hybrid. The hybridization can be carried out under isothermal conditions or preferentially with gradual cooling.

27 Claims, 2 Drawing Sheets

FOREIGN PATENT DOCUMENTS

| | | |
|---|---|---|
| 85870065.1 | 5/1985 | European Pat. Off. |
| 86114590.2 | 10/1986 | European Pat. Off. |
| 87300195.2 | 1/1987 | European Pat. Off. |
| PCT/US86/-02788 | 12/1986 | WIPO |

OTHER PUBLICATIONS

Studencki, et al., Am J Hum Genet 37:42-51, 1985.
Orkin, et al., J. Clin. Invest. (The American Society for Clinical Investigation, Inc.) vol. 71, Mar., 1983.
Fischer, et al., Proc. Natl. Acad. Sci. U.S.A. vol. 80, pp. 1579-1583, Mar. 1983 Biochemistry.
Winter, et al., Proc. Natl. Acad. Sci. U.S.A. vol. 82, pp. 7575-7579, Nov., 1985 Biochemistry.
Paul H. Edelstein et al., Journal of Clinical Microbiology, Jun. 1987, pp. 1022-1026, Retrospective Study of Gen-Probe Rapid Diagnostic System, etc.
Nell S. Lurain, et al., Journal of Clinical Microbiology, Nov. 1986, pp. 724-730; Rapid Detection of Cytomegalovirus in Clinical Specimens, etc.
Thomas A. Drake, et al., Journal of Clinical Microbiology, Aug. 1987, pp. 1442-1445; Rapid Identification of Mycobacterium Avium Complex, etc.
Gonzalez & Hanna, Diagn. Microbiol. Infect. Dis., vol. 8, No. 2, pp. 69-77 (Dec. 1987).
Paul H. Edelstein, Journ. of Clinical Microbiolgby, Mar. 1986, pp. 481-484, vol. 23, No. 3., Evaluation of the Gen-Probe DNA Probe for Detection, etc.
T. E. Kiehn, et al., Journ. Clinica Microbiology, Aug. 1987, pp. 1551-1552; vol. 25, No. 8, Rapid Identification Using a Specific DNA Probe, etc.

* The temperatures indicated are the melting temperatures of the match and mismatch hybrids in the first example.

ASSAY FOR POLYNUCLEOTIDES EMPLOYING OLIGONUCLEOTIDES TO ELIMINATE UNDESIREABLE CROSS REACTIONS

This application is a continuation of application Ser. No. 07/554,088, filed Jul. 17, 1990, now abandoned which is a continuation of application Ser. No. 080,331 filed Jul. 31, 1987, now abandoned.

FIELD OF THE INVENTION

The present invention relates to an assay for a desired nucleotide sequence (the "target nucleotide sequence") which may be present together with other nucleotide sequences (the "non-target nucleotide sequences"), the latter being capable of interfering in the assay for the former to result in potentially false qualitative or quantitative results.

TECHNOLOGY REVIEW

It has long been recognized that unique or misexpressed nucleotide sequences in a polynucleotide can be detected by hybridization with a nucleotide multimer probe. This technique permits the early detection of infectious organisms such as bacteria, viruses, etc.; genetic diseases such as sickle cell anemia; and various cancers. The probe (referred to as the "target probe") is selected with a nucleotide sequence complementary (usually exactly complementary) to the nucleotide sequence which is desired to be detected (the "target nucleotide sequence"). Following hybridization of the probe with the target polynucleotide, any target probe/polynucleotide hybrids which have formed are typically separated from unhybridized probe. The amount of probe in either of the two separated mediums is then tested to provide a qualitative or quantitative measurement of the amount of target originally present.

However, in many assays there may be one or more non-target polynucleotides present which have a nucleotide sequence closely related to that of the target sequence (for example differing in only 1 to 5 nucleotides). In such cases the non-target polynucleotide may then interfere with the assay, by hybridizing with at least some of the target probe, to produce false qualitative or quantitative results. This problem is exacerbated where the probe sequence is selected to permit assaying of various species of organisms within a particular genus, each species of which contains the target nucleotide sequence or one very closely related thereto (e.g., differing by only one nucleotide).

A solution to the foregoing type of interference has been suggested, for example by Wallace et al., Proc. Natl. Acad. Sci. USA, 80, 278–282 (1983) where the precise control of stringency is used to detect single nucleotide differences. Using oligonucleotide probes which were only 19 nucleotides in length and precisely controlling stringency Wallace et al. was able to discriminate sickle anemia associated hemoglobin DNA and normal DNA bound to nitrocellulose which differed by only a single point mutation. Such a method takes advantage of the fact that the target probe/target polynucleotide hybrid will have a higher melting temperature than the target probe/non-target polynucleotide hybrid, since the target probe is intentionally selected with a nucleotide sequence more closely complementary to that of the target nucleotide sequence, than to any related nucleotide sequence of any non-target polynucleotide which might be present. In these types of assays then, polynucleotides bound to nitrocellulose are hybridized with polynucleotide probes at a controlled temperature which ideally is between the respective melting temperatures of the probe/target polynucleotide hybrid and the probe/non-target polynucleotide. However, the foregoing melting temperatures may differ by only about 2°–3° C.

Thus, a serious difficulty with the foregoing method is that it requires stringent control of temperature, and even then either typically permits a large amount of interference from the non-target polynucleotide (i.e., relatively large amounts of probe are hybridized with non-target polynucleotide), or results in low extents of hybridization between the target probe and target polynucleotide, thereby potentially leading to false qualitative results. Furthermore, for quantitative results an even higher degree of temperature control is required, since close to the same temperature must be maintained during hybridizations in both assays to establish a standard curve, and an assay of an unknown sample.

DEFINITIONS

As used in this disclosure and claims, the following terms are defined as:

nucleotide: a subunit of a nucleic acid consisting of a phosphate group, a 5 carbon sugar and a nitrogen containing base. In RNA the 5 carbon sugar is ribose. In DNA, it is 2-deoxyribose.

nucleotide multimer: a chain of nucleotides linked by phosphodiester bonds or analog thereof.

oligonucleotide: a nucleotide multimer generally about 10 to about 100 nucleotides, but which may be 200 or more nucleotides in length. They are usually synthesized from nucleotide monomers or obtained by enzymatic means.

polynucleotide: a nucleotide multimer generally more than about 100 nucleotides in length.

target nucleotide sequence: is a nucleotide sequence for which an assay is being performed. It may cover a group of closely related nucleotide sequences (e.g., differing by only one nucleotide such as various organisms within a genus).

non-target nucleotide sequence: is one or more nucleotide sequences which may interfere with an assay for the target nucleotide sequence using a selected probe because of a high degree of sequence homology with the target nucleotide sequence. Generally, but not necessarily, the target and non-target nucleotide sequences are on distinct nucleotide multimers. The non-target probe may be complementary with only a portion of the non-target sequence and may overlap a portion of both the non-target sequence and adjacent nucleotides. It is only necessary that the non-target probe hybridize with enough of the non-target sequence to prevent cross reaction with the target probe.

nucleotide multimer probe: a probe which is itself a nucleotide multimer (usually, but not necessarily, an oligonucleotide), selected to hybridize preferentially with a target, or non-target, nucleotide multimer.

melting temperature: with reference to a nucleotide multimer hybrid, is that temperature at which one half of that hybrid is denatured.

SUMMARY OF THE INVENTION

The present invention then, provides a means in an assay for a target nucleotide sequence using a selected probe (the "target probe"), by which interference from one or more non-target nucleotide sequences can be reduced. This is accomplished by providing one or more other probes (the "non-target probe") which can hybridize with at least a portion of the non-target sequences which may be present, so as to reduce the amount of the non-target sequences which might otherwise hybridize with the target probe.

Preferably then, the present invention provides an assay, and a kit useful in performing such an assay, for detecting a target polynucleotide sequence which may also contain a non-target polynucleotide sequence. The medium is contacted with distinct, target and non-target, nucleotide multimer probes under hybridizing conditions. This allows the target probe to hybridize with the target present (i.e., the target that may be present). However, since the target and non-target multimers are closely related, the probe can also incidentally hybridize with non-target polynucleotide sequences present. The non-target probe or probes are selected so that under such hybridizing conditions, it will hybridize with non-target polynucleotide sequence present, so as to reduce the extent of any target probe/non-target hybridization which may occur absent the non-target probe, while not unduly reducing any target probe/target hybridization (i.e., not reducing it to such an extent as to make the assay unworkable in a practical situation).

This invention can be utilized with any of the standard hybridization methods. Generally this employs formation of the target probe/target hybrid on a surface or in solution in a manner so as to permit detection of the target probe/target hybrid without detecting undue quantities of the unhybridized target probe. This can typically be done using the following procedures:

1. Formation of the target probe/target hybrid on the surface of a solid support followed by segregation of said hybrid away from the unhybridized target probe.
2. Formation of the target probe/target hybrid in solution followed by segregation of said hybrid and said unhybridized target probe.

In order to determine either quantitatively or qualitatively, the amount of target nucleotide sequence present employing these procedures, the amount of target probe hybridized or unhybridized can be determined and related to the amount of hybrid formed. Typically, the amount of target probe in the hybridized form is determined except in those cases where the target probe displaces a previously hybridized labeled probe (see for example Clin. Chem. 32, 1696–1701 (1986)).

This method, however, is not limited to hybridization procedures which require a separation step. For example, as improved homogeneous assay methods become available the invention procedure described here will also be useful in homogeneous assay formats.

This invention can be employed in several forms. The requirement being that at some point in the hybridization assay the non-target probe or probes are able to hybridize with the non-target sequence without significantly hybridizing with the target sequence. Such "capping" of the non-target sequence may occur either before, during or after the hybridization between the target probe and the target sequence. A preferred embodiment is to employ said "capping" during the hybridization between the target probe and target sequence. This use of the invention can be carried out in several formats. These include:

1. Iso-Thermal. Hybridization occurs at a constant temperature.
2. Slow Cool. The hybridization occurs over a decreasing temperature range generally including the melting temperature (Tm) of the target probe/target nucleotide sequence hybrid.

The non-target probe may, alternatively be added before the target probe to provide for capping of non-target sequences before the target probe is added. It is also suitable to carry out the target probe/target sequence hybridization at high temperatures and/or under high stringency conditions and then add non-target probe to prevent target probe/non-target sequence hybridization as the temperature and/or stringency is lowered.

Preferably, the probes are selected such that the melting temperature of the non-target probe/non-target sequence hybrid, is greater then the melting temperature of the target probe/non-target sequence hybrid. Hybridization conditions are preferably established by first heating the medium to denature at least the probes and any target sequence present (and preferably to a temperature which will denature all nucleotide multimers present), then gradually cooling the medium to a temperature such that the target probe can hybridize with the target sequence (and preferably at which all hybridizations are complete). During cooling, non-target probe can hybridize with non-target sequence to prevent cross reaction when the temperature at which the target probe cross reacts with non-target sequence is subsequently reached. In one aspect of the invention, hybridizing conditions are established by the foregoing means with all polynucleotides present in a liquid medium, absent any solid phase support on which the liquid medium is absorbed. Such a solid phase would include a solid support such as nitrocellulose.

In another aspect of the invention, the target probe is labeled with one or more atoms or molecules which lend themselves to ready detection. Such labels can include, but are not limited to, radiolabels, enzymes, chemiluminescent labels, colorimetric labels, or fluorescent labels. Furthermore, the step of testing for the presence of target probe, as already described, preferably involves segregating (and preferably separating) any target probe hybridized with nucleotide multimers, from target probes not so hybridized. Such segregation (or separation) can be accomplished by selective absorption of polynucleotide hybrids on a solid support such as hybroxyapatite using a procedure such as described in Kohne, D. E. and Britten, R. J., "Nucleic Acid Research" Vol. 2, p. 500–12 (1971) which is incorporated herein by reference. However, where the target nucleotide sequence is on a polynucleotide of substantially greater length than the target probe (which will be the typical situation where the polynucleotide originates from a clinical sample), separation may be preferably accomplished by selectively immobilizing the longer target sequence and hybridized target probe on polycationic particles through ionic attraction.

DRAWINGS

Embodiments of the invention will now be described with reference to FIGS. 1 and 2.

DETAILED DESCRIPTION OF EMBODIMENTS OF THE INVENTION

EXAMPLE I

To demonstrate the present invention, four synthetic oligodeoxynucleotides were prepared, namely "PROBE", "TARGET", "MIS-PROBE", and "MIS-TARGET". The probe is a 35 base sequence which is an exact complement to the "TARGET". MIS-TARGET is the TARGET sequence with two substitutions (mismatches): position 12 has an A substituted for a T and position 24 has a C substituted for a G. MIS-PROBE is the exact complement of MIS-TARGET. The 2 substitutions are placed ⅓ of the distance from the end of the probe. The purine and pyrimidine content is constant among all the sequences as is the G+C content.

The probes were synthesized using an Applied Biosystems, Inc. Model 380A DNA Synthesizer and purified using standard methods (Tetrahedron, 39 3–22 (1983)).

The sequence of the above oligonucleotides are as follows:

| | |
|---|---|
| PROBE: | 5' CAG TCA AAC TCT AGC CAT TAC CTG CTA AAG TCA TT 3' |
| TARGET: | 3' GTC AGT TTG AGA TCG GTA ATG GAC GAT TTC AGT AA 5' |
| MIS-PROBE: | 5' CAG TCA AAC TCA AGC CAT TAC CTC CTA AAG TCA TT 3' |
| MIS-TARGET: | 3' GTC AGT TTG AGT TCG GTA ATG GAG GAT TTC AGT AA 5' |

In the experiments which follow, PROBE and MIS-PROBE act as nucleotide multimer probes, while TARGET and MIS-TARGET each acts as either a target or a non-target nucleotide multimer (the entire sequence of each being either a target or non-target nucleotide sequence).

Figure 1:
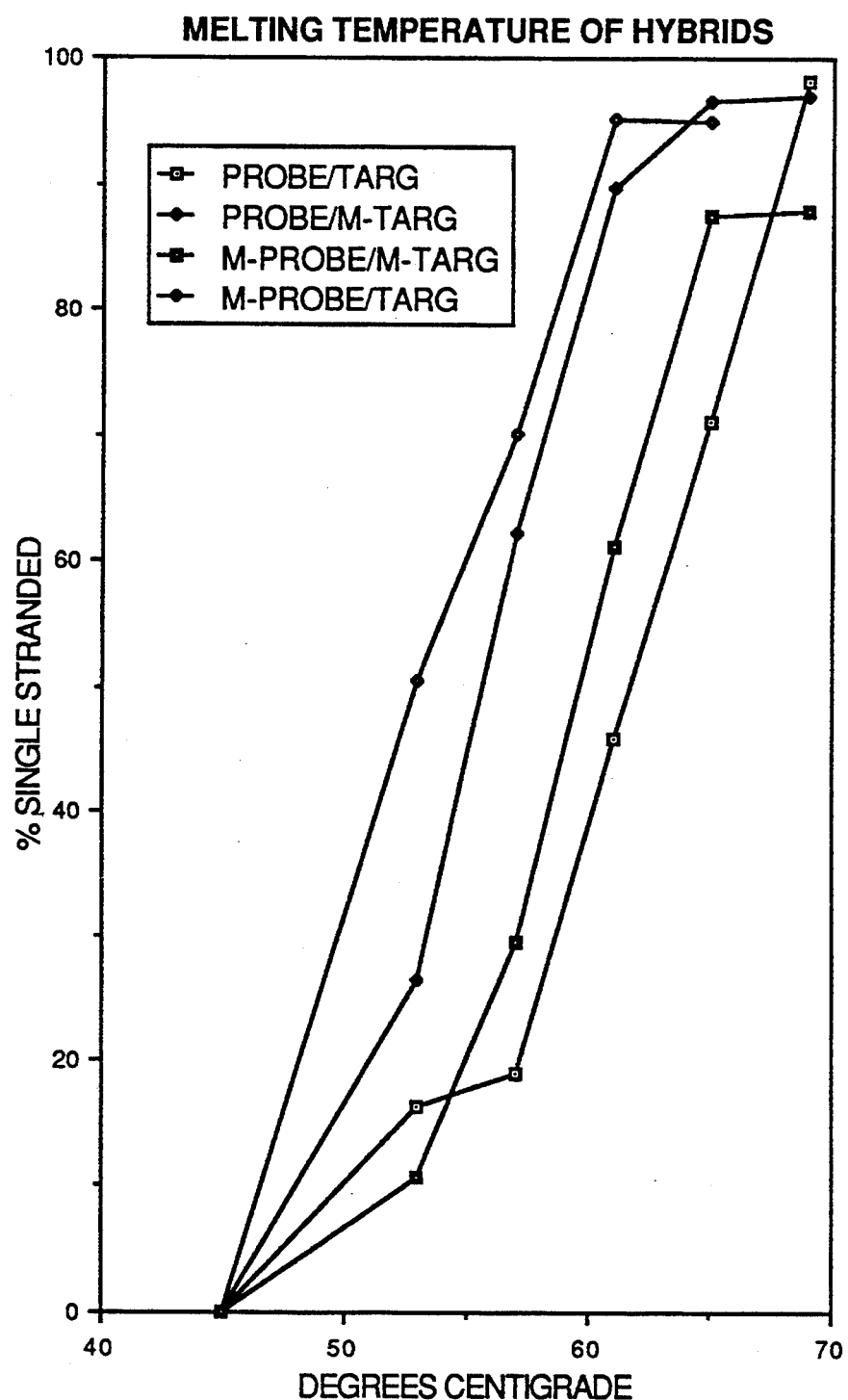
FIG. 1 is a graph illustrating thermal stability of the hybrids formed in the experiment described below.

The thermal stability of each of the probes with each of the target multimers was first investigated. The PROBE and MIS-PROBE were kinase end labeled using T4 kinase $^{32}$p and gamma adenosine triphosphate (ATP) and then each was independently hybridized with both the TARGET and MIS-TARGET (for a total of four independent hybridizations) at 50° C. in 0.48M phosphate buffer pH 6.8, 0.1% sodium dodecyl sulfate (SDS). Aliquots (10 ul) of the solutions were then diluted in 3 mls of a "reaction buffer" consisting of 0.1M phosphate buffer pH 6.8 and, 0.1% SDS, and heated for 5 minutes at various temperatures as indicated in FIG. 1. The percentage of hybridized probe was determined by binding to hydroxyapatite at 45° C. in 0.08M phosphate buffer pH 6.8, 0.02% SDS, using the method of Kohne, supra. The results are plotted in the FIG. 1 as percent of single stranded nucleotide remaining. The temperature at which half of the probe remains hybridized and half of the probe is single stranded, is known as the melting temperature (Tm) and is used as the measure of thermal stability. When the exact complement (target multimer) of each probe was replaced by the non-target multimer (thus replacing each probes complement by a nucleotide multimer differing in only two bases therefrom) a 6°–7° C. lowering of the Tm resulted.

Figure 2:
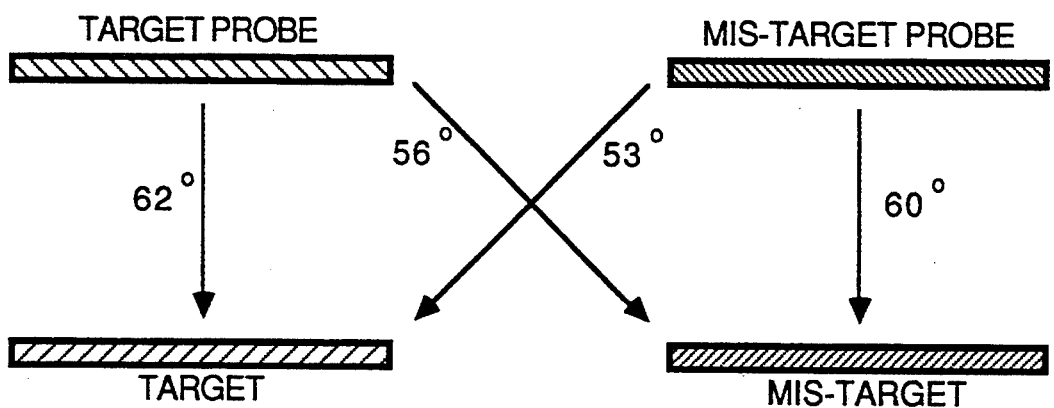
FIG. 2 is a diagram illustrating the relationship of the Tm for various possible hybrids.

FIG. 2 illustrates the hybridization Tm for the various reactions and cross reactions that can occur.

Referring to FIG. 1, it will be seen that in an assay for either one of TARGET or MIS-TARGET (the one for which the assay is desired being referred to as the "target nucleotide multimer" and the other one being the "non-target nucleotide multimer"), where both may be present together, it would be difficult to select a temperature at which most of the target multimer would be hybridized with its complementary probe (the "target probe") without at the same time having a substantial proportion of the target probe hybridized with the non-target multimer. Thus, the non-target nucleotide multimer would interfere with the assay of the target nucleotide multimer, unless a temperature was selected where only a small portion of the target nucleotide multimer is hybridized.

The present invention substantially reduces interference which may occur from a non-target nucleotide sequence, and thus can eliminate the need for stringent temperature control, by having present during hybridization both a target probe and a non-target probe.

To illustrate the foregoing, a further experiment was performed. The PROBE and MIS-PROBE were mixed in reaction buffer, in the molar ratios shown in TABLE 1 below. Using a water bath, the reactions were heated to 70° C. for 5 minutes and then slowly cooled to 50° C. over a period of 2 hours. Incubation at 50° C. was then continued for 1 hour. The initial heating of the reactions assured that all sequences were single stranded (i.e., "denatured") at the start; the final 50° C. temperature allowed for any combination of probe and target sequence hybridization to occur since it is well below all Tm's. As will be illustrated later, gradual cooling favored the pairing of exact complements over mismatched complements as the temperature slowly decreased through their respective Tm's. Reactions were assayed by binding to hydroxyapatite as described previously.

To obtain the results in TABLE 1(A), the TARGET PROBE was labeled, and TARGET and MIS-TARGET were the target and non-target nucleotide multimers, respectively, while the MIS-PROBE was unlabeled. The results in Table 1(A) show that: (1) hybridization of the target probe and target multimer (reactions A–D) is not unduly reduced by the presence of even up to a 4× excess of non-target probe; (2) excess unlabeled probe under the same conditions competes roughly as might be expected (within the limits of experimental uncertainty) with the labeled probe (reactions E–G); (3) target probe hybridizes significantly with the non-target (reaction H), but this hybridization is very effectively removed when even a relatively low amount of non-target probe (1:1 molar ratio with target probe) is present (reactions I–K); and (4) with both probes and both multimers mixed together, the non-target probe apparently hybridizes with non-target multimer so as to reduce the extent of any target probe/non-target multimer hybridization which might occur absent the non-target probe, while hardly affecting the target probe/target multimer hybridization (and certainly not unduly reducing it) (reactions L–O).

Table 1(B) shows the results for the same experiment done with mis-TARGET PROBE as the labeled probe, and TARGET PROBE as the unlabeled probe. Thus, MIS-TARGET and TARGET can be regarded now as the target and non-target nucleotide multimers, respectively. The results also support conclusions (1)-(4) above. In particular, reactions A and H in TABLE 1B represent a situation where the two target multimers could not be distinguished by the single labeled probe (82% vs 78% hybridization). The presence of the TARGET PROBE (used as a non-target "capping" probe here) instead promotes a clear difference in hybridization extent. In this case the desired hybridization of the labeled MIS-PROBE with the MIS-TARGET was 56%, vs 0% for the labeled MIS-PROBE and TARGET (reactions D and K).

An experiment was done to compare the gradual cool method with the isothermal procedure. Reactions A-D and H-K in Table 1(A) were repeated except that the temperature was immediately lowered to an incubation temperature of 50° C. or 55° C. (by placing tubes containing the reaction solutions into water baths of those respective temperatures), as indicated in TABLE 2, after the 70° C. pre-heating step. Incubation was then continued at the incubation temperature for 2 hours and the reactions were assayed on hydroxyapatite as described previously. The results are shown in TABLE 2. It is apparent from TABLE 2 that when cooling was immediate, the amount of target probe/target multimer hybridization is somewhat reduced in the presence of the "capping" MIS-TARGET PROBE (reactions A-D), while the amount of TARGET PROBE/MIS-TARGET multimer hybridization is somewhat increased (reactions H-K). Thus a gradual cooling as part of establishing hybridization, appears to be advantageous in the method of the present invention.

interference from a non-target nucleotide sequence (typically on another nucleotide multimer) can be reduced by providing a non-target probe which forms a hybrid with the non-target nucleotide multimer with a higher Tm than the Tm for the target probe/non-target probe which forms a hybrid with the non-target nucleotide multimer hybrid. Thus, in an assay for any given target nucleotide sequence, potential interference from a closely related non-target nucleotide sequence can be reduced. Furthermore, as has been shown, if hybridizing conditions are established by gradual cooling, the foregoing beneficial effect is further enhanced.

The ratio of non-target probe to target probe can vary substantially. It is preferred that the ratio is no greater than 9 to 1. The particularly preferred ratio is no greater than 4 to 1.

The amount of non-target probe used can vary over a wide range and yet provide the improved results described above. However, it is preferred that the non-target probe be present in a molar amount about equal to the amount of non-target sequence and it is particularly preferable in a molar amount which is in excess of the non-target sequence present in the sample. This can be accomplished by using an amount of probe which is greater than the amount of target and non-target RNA sequences in the sample.

Although in the above experiments the target and non-target nucleotide sequences consisted of the entire length of the target and non-target nucleotide multimers, it will be apparent that this need not necessarily be so. In fact, in most clinical applications both sequences

TABLE 1

Effect of Probe Ratios on Competition

|  | A | B | C | D | E | F | G | H | I | J | K | L | M | N | O |
|---|---|---|---|---|---|---|---|---|---|---|---|---|---|---|---|
| 1A | | | | | | | | | | | | | | | |
| LABELED PROBE | 1* | 1 | 1 | 1 | 1 | 1 | 1 | 1 | 1 | 1 | 1 | 1 | 1 | 1 | 1 |
| UNLABELED PROBE | | | | | 1 | 2 | 4 | | | | | | | | |
| NON-TARGET PROBE | | 1 | 2 | 4 | | | | | 1 | 2 | 4 | | 1 | 2 | 4 |
| Target | 1 | 1 | 1 | 1 | 1 | 1 | 1 | | | | | 1 | 1 | 1 | 1 |
| Mis-Target | | | | | | | | 1 | 1 | 1 | 1 | 1 | 1 | 1 | 1 |
| % Hybridization | 84 | 70 | 76 | 76 | 31 | 20 | 11 | 40 | 5 | 3 | 2 | 85 | 79 | 71 | 78 |
| Normalized % Hybridization | 100 | 83 | 90 | 90 | 37 | 24 | 13 | 48 | 6 | 4 | 2 | 101 | 94 | 85 | 93 |
| 1B | | | | | | | | | | | | | | | |
| LABELED MIS PROBE | 1 | 1 | 1 | 1 | 1 | 1 | 1 | 1 | 1 | 1 | 1 | 1 | 1 | 1 | 1 |
| UNLABELED MIS PROBE | | | | | 1 | 2 | 4 | | | | | | | | |
| TARGET PROBE | | 1 | 2 | 4 | | | | | 1 | 2 | 4 | | 1 | 2 | 4 |
| Mis-Target | 1 | 1 | 1 | 1 | 1 | 1 | 1 | | | | | 1 | 1 | 1 | 1 |
| Target | | | | | | | | 1 | 1 | 1 | 1 | 1 | 1 | 1 | 1 |
| % Hybridization | 82 | 54 | 54 | 56 | 37 | 22 | 13 | 78 | 11 | 0 | 0 | 80 | 68 | 56 | 52 |
| Normalized % Hybridization | 100 | 66 | 66 | 68 | 45 | 27 | 16 | 95 | 13 | 0 | 0 | 98 | 83 | 71 | 63 |

*Footnote: Corresponds to 0.1 p moles of probe in a 10 μl hybridization reaction.

TABLE 2

Temperature Effect

|  | A | B | C | D | H | I | J | K |
|---|---|---|---|---|---|---|---|---|
| LABELED PROBE | 1* | 1 | 1 | 1 | 1 | 1 | 1 | 1 |
| "CAPPING" MIS PROBE | | 1 | 2 | 4 | | 1 | 2 | 4 |
| Target | 1 | 1 | 1 | 1 | | | | |
| Mis-Target | | | | | 1 | 1 | 1 | 1 |
| % Hybridization | 84 | 70 | 76 | 76 | 40 | 5 | 3 | 2) |
| | | | | | | | | ) Slow Cool 70° → 50° |
| Normalized % Hybridization | 100 | 83 | 90 | 90 | 48 | 6 | 4 | 2) |
| % Hybridization | 80 | 56 | 43 | 42 | 45 | 16 | 9 | 4) |
| | | | | | | | | ) Isothermal 50° |
| Normalized % Hybridization | 100 | 70 | 54 | 53 | 56 | 20 | 11 | 5) |
| % Target Hybridization | 80 | 66 | 62 | 50 | 33 | 9 | 4 | 3) |
| | | | | | | | | ) Isothermal 55° |
| Normalized % Hybridization | 100 | 83 | 78 | 63 | 41 | 11 | 5 | 4) |

*Footnote: Corresponds to 0.1 p mole of probe in a 10 μl hybridization reaction.

It has been illustrated above than, in an assay for a target nucleotide sequence using a target probe, that will be only a portion of the length of substantially longer target and non-target polynucleotides. Illustration of such a clinical assay is the following example.

EXAMPLE II

In this case the synthetic target probe and non-target probe were hybridized to cellular RNA, as would be the case in a clinical assay. This system consisted of Neisseria gonorrhoeae (gon RNA as the desired target) and Neisseria meningitidis (men RNA as the undesired mismatched target). Probes were synthesized which were complementary to both RNA species except for a two base mismatch as in EXAMPLE 1. The probe sequences were as follows:

gon probe: 5' GAG GAT TCC GCA CAT GTC AAA ACC AGG TAA 3'
men probe: 5' GAG GAT TCC GTA CAT GTC AAG ACC AGG TAA GG 3'

The probes were synthesized as in Example I. Probe sequences are obtained by doing sequence alignments of closely related organisms and selecting regions which are specific to the desired organism.

The Tm's of each combination of probe and target RNA were determined: gon probe plus gon RNA 59.2° C., gon probe plus men RNA 48.2° C., men probe plus men RNA 61.5° C. and men probe plus gon RNA 55° C. As was the case in the first working example above, exact match hybridization had a TM approximately 6°–10° above the corresponding mismatched hybridizations.

Hybridization assays were performed which were analogous to the isothermal 55° C. condition of Table 2 with an additional slow cooling step from 55° C.→40° C. (In this case hybridizations were done in 0.48M phosphate buffer pH 6.8, 0.5% SDS and the hydroxyapatite separations were done in 0.12M phosphate buffer pH 6.8, 0.02% SDS at 40° C.) The reactions were heated at 70° C. for 5 minutes to ensure complete denaturation of all components, immediately cooled to 55° C. and incubated 15 hours, slow cooled to 40° C. over a period of 4 hours and then incubation at 40° C. continued for another hour. These reactions were incubated longer than in the first example and with a larger excess of probe since these probes were known to hybridize slower.

The results in Table 3 show the same capping effect of the non-target probe (men) on the non-target RNA as was seen in the first example. Hybridization of target probe to target RNA was not seriously decreased in the presence of a two-fold excess of non-target probe (reaction D), while the undesired cross hybridization of target probe to non-target RNA, though small, was eliminated completely at a 1:1 ratio of non-target capping probe to target probe (reaction J).

TABLE 3

|  | A | B | C | D | H | I | J | K |
|---|---|---|---|---|---|---|---|---|
| gon target probe | 3* | 3 | 3 | 3 | 3 | 3 | 3 | 3 |
| men non-target probe |  | 2 | 3 | 6 |  | 2 | 3 | 6 |
| gon target (RNA) | 1 | 1 | 1 | 1 |  |  |  |  |
| men non-target (RNA) |  |  |  |  | 1 | 1 | 1 | 1 |
| % of maximum possible hybridization | 53 | 48 | 38 | 52 | 10 | 1 | 0 | 0 |
| Normalized % of maximum possible hybridization | 100 | 91 | 72 | 98 | 19 | 2 | 0 | 0 |

*Footnote: corresponds to 0.3 p mole of probe in 30 microliter hybridization reaction.

EXAMPLE III

Another experiment was done to determine the effectiveness of capping, using large probe excesses and low concentrations of RNA—as might be typical in a clinical assay. In this example the probes and RNA's were mixed in the ratios indicated (in 0.48M phosphate buffer pH 6.8, 0.5% SDS, 1 mM EDTA, 1 mM EGTA), heated at 70° C. for 5 minutes, slow cooled at 55° C. over a period of 1¼ hours, incubated at 55° C. for 2 hours, slow cooled to 45° C. over a period of 30 minutes and then incubated at 45° C. for 30 minutes. Hybridization were then separated on hydroxyapatite as above. This incubation scheme allowed for maximum discrimination of exact match hybridizations since there was slow cooling above the intermediate (stringent) temperature of 55° C. and a prolonged incubation at that temperature.

As seen in Table 4 the capping (non-target) probe again completely eliminated the cross reaction of target probe and non-target RNA while decreasing the specific hybridization (target probe/target RNA) only 26%.

TABLE 4

| gon probe | 15* | 15 | 15 | 15 |
|---|---|---|---|---|
| men probe |  | 30 |  | 30 |
| gon RNA | 1 | 1 |  |  |
| men RNA |  |  | 1 | 1 |
| % of maximum possible hybridization | 129 | 95 | 5 | 0 |
| Normalized % of maximum possible hybridization | 100 | 74 | 4 | 0 |

Footnote: corresponds to 0. 2 p mole of probe in 100 microliter hybridization reaction.

It will also be of course appreciated from the foregoing that the target probe could be labeled by means of many of the labels well known in the art. Furthermore, a kit can be assembled which contains either separately, or in admixture, the target and non-target probes, for use in ascertaining the presence of a target nucleotide sequence in a medium which may also have present a related non-target nucleotide sequence.

As will be evident to those skilled in the art, various modifications and alterations to the embodiments described above are possible. Accordingly, the scope of the present invention is not limited to the embodiments described in detail above.

I claim:

1. An assay for a target nucleotide sequence in a sample comprising the steps of:
   (a) providing a target probe 10 to 100 nucleotides in length having a selected nucleotide sequence sufficiently complementary to said target nucleotide sequence to hybridize with said target nucleotide sequence under hybridizing conditions to form a first hybrid complex, and sufficiently complementary to a non-target nucleotide sequence to hybridize with said non-target nucleotide sequence under said hybridizing conditions to form a second hybrid complex separate and distinct from said first hybrid complex, the melting temperature of said first hybrid complex being higher than that of said second hybrid complex, said non-target nucleotide sequence differing from said target nucleotide sequence by 1 to 5 nucleotides, (b) providing a non-target probe 10 to 100 nucleotides in length having a second selected nucleotide sequence, said non-target probe nucleotide sequence differing from said target probe nucleotide sequence by 1 to 5 nucleotides, said non-target probe nucleotide sequence being sufficiently complementary to said non-target nucleotide sequence to hybridize with said non-target nucleotide sequence under said hybridizing conditions to form a third hybrid complex, the melting temperature of said third hybrid complex being higher than that of said second hybrid complex, (c) contacting said sample with said target probe and at least one said non-target probe under said hybridizing conditions, wherein under said hybridizing conditions the formation of said third hybrid complex reduces the formation of said second hybrid complex, and, (d) assaying for hybridization of said target probe with said sample.

2. A method as defined in claim 1 wherein said hybridizing conditions are established by first heating the medium to denature at least said target and non-target probes and any target nucleotide sequence present, then cooling the medium with an external heat exchange medium the temperature of which is decreased so that said target probe can hybridize with said target nucleotide sequence under non-isothermal hybridizing conditions.

3. A method as defined in claim 1 wherein hybridization occurs at a fixed temperature.

4. A method as defined in claim 1, 2 or 3 wherein the hybridization conditions are established with said target and non-target probes present in a liquid medium, absent any solid phase support.

5. A method as defined in claim 1, 3 or 4 wherein the target and non-target nucleotide sequences are bound to a solid support at the time of hybridization.

6. A method as defined in claims 1, 2 or 3 wherein said target probe is labeled and said non-target probe is unlabeled, the molar ratio of unlabeled probe to labeled probe is no greater than 9 to 1, and wherein the hybridizing conditions are established with said target and non-target probes present in a liquid medium absent any solid phase support on which the liquid medium is absorbed.

7. A method as defined in claims 1, 2 or 3 wherein said target probe is labeled and said non-target probe is unlabeled, the molar ratio of unlabeled said non-target probe to labeled said target probe is no greater than 9 to 1, and wherein the hybridizing conditions are carried out with the target and non-target nucleotide sequences bound to a solid support.

8. A method as defined in claim 1, 2 or 3 wherein the molar ratio of non-target probe to target probe is no greater than 4 to 1.

9. An assay in a liquid medium for a target nuceotide sequence in a sample comprising the steps of:

(a) providing a target probe 10 to 100 nucleotides in length having a selected nucleotide sequence sufficiently complementary to said target nucleotide sequence to hybridize with said target nucleotide sequence under hybridizing conditions to form a first hybrid complex, and sufficiently complementary to a non-target sequence to hybridize with said non-target nucleotide sequence, under said hybridizing conditions to form a second hybrid complex separate and distinct from said first hybrid complex, the melting temperature of said first hybrid complex being higher than that of said second hybrid complex, said non-target nucleotide sequence differing from said target nucleotide sequence by 1 to 5 nucleotides, (b) providing a non-target probe 10 to 100 nucleotides in length having a second selected nucleotide sequence, said non-target probe nucleotide sequence differing from said target probe nucleotide sequence by 1 to 5 nucleotides, said non-target probe nucleotide sequence being sufficiently complementary to said non-target nucleotide sequence to hybridize with said non-target nucleotide sequence under said hybridizing conditions to form a third hybrid complex, the melting temperature of said third hybrid complex being higher than that of said second hybrid complex, (c) contacting said sample in a liquid medium with said target probe and at least one said non-target probe under said hybridizing conditions, wherein under said hybridizing conditions the formation of said third hybrid complex reduces the formation of said second hybrid complex and, (d) assaying for hybridization of said target probe with said sample.

10. A method as defined in claim 9 wherein said target and non-target probes are selected such that said third hybrid complex has a greater number of complementary nucleotides than said second hybrid complex.

11. A method as defined in claim 9 wherein hybridizing conditions are established by first heating the liquid medium to denature at least said target and non-target probe and any target nucleotide present, then cooling the liquid medium so that said target probe can hybridize with target nucleotide under non-isothermal hybridizing conditions.

12. A method as defined in claim 11 wherein the hybridizing conditions are established with the target nucleotide present in the liquid medium, absent any solid phase support on which the liquid medium is absorbed.

13. A method as defined in claim 9 wherein hybridizing conditions are established by first heating the medium to a temperature which will denature at least any said first hybrid complex, then cooling the medium with an external heat exchange medium the temperature of which is decreased so that the target probe can hybridize with the target sequence under non-isothermal hybridizing conditions.

14. A method as defined in claim 11 wherein the molar ratio of said non-target probe to said target probe, is no greater than 9 to 1, and wherein the hybridizing conditions are established with the target nucleotide present in the liquid medium absent any solid phase support on which the liquid medium is absorbed.

15. A method as defined in claim 9, 10, 11 or 12 wherein the molar ratio of non-target probes to target probes is no greater than 4 to 1.

16. A method as defined in claim 9 wherein the target nucleotide sequence is from the group consisting of RNA and DNA.

17. A method as defined in claim 9, or 13 wherein the assaying step comprises first segregating any said first, second, or third hybrids from unhybridized labeled probe, then identifying the presence of label in said hybrids.

18. A method as defined in claim 9, or 13 wherein the target and non-target nucleotide sequences are present on polynucleotides of greater length than said target and non-target probes, and the method further comprises:
- (a) contacting the liquid medium with a polycationic solid support capable of noncovalently binding polynucleotides and hybrids thereof, so as to separate said target probe hybridized with any polynucleotide from any said target probe not so hybridized;
- (b) segregating the solid support from the liquid medium containing said target probe not so hybridized; and
- (c) detecting the presence of any label bound to the solid support.

19. A kit useful for assaying a target nucleotide sequence in a sample, comprising:
- (a) a labeled target probe 10 to 100 nucleotides in length having a selected nucleotide sequence sufficiently complementary to said target nucleotide sequence to hybridize with said target nucleotide sequence under hybridizing conditions to form a first hybrid complex, and sufficiently complementary to a non-target sequence to hybridize with said non-target nucleotide sequence under said hybridizing conditions to form a second hybrid complex separate and distinct from said first hybrid complex, the melting temperature of said first hybrid complex being higher than that of said second hybrid complex, said non-target nucleotide sequence differing from said target nucleotide sequence by 1 to 5 nucleotides, and
- (b) an unlabelled non-target probe 10 to 100 nucleotides in length having a second selected nucleotide sequence, said non-target probe nucleotide sequence differing from said target probe nucleotide sequence by 1 to 5 nucleotides, said non-target probe nucleotide sequence being sufficiently complementary to said non-target nucleotide sequence to hybridize with said non-target nucleotide sequence under said hybridizing conditions to form a third hybrid complex, the melting temperature of said third hybrid complex being higher than that of said second hybrid complex, wherein under said hybridizing conditions the formation of said third hybrid complex reduces the formation of said second hybrid complex.

20. A kit as defined in claim 19 wherein said target and non-target probes are selected such that unlabeled said third hybrid complex will have a greater number of complementary nucleotides than labeled said second hybrid complex.

21. A kit as defined in claim 20 wherein the probes are oligonucleotides which differ by one to three nucleotides only.

22. A kit as defined in claim 20, or 21 wherein the molar ratio of said non-target probe to said target probe is no greater then 9 to 1.

23. A kit as defined in claim 20, or 21 wherein said probes can hybridize with a polynucleotide from the group consisting of RNA and DNA.

24. A kit as defined in claim 20 or 21 wherein the label of the labeled probe is selected from a group consisting of radiolabels, enzymes, chemiluminescent labels, colorimetric labels, and fluorescent labels.

25. A method as defined in claim 1 wherein the target probe is immobilized on a solid support at the time of hybridization.

26. A method as defined in claim 9 wherein hybridization occurs at a fixed temperature.

27. A kit as defined in claim 20 or 21 wherein the molar ratio of said non-target probe to said target probe is no greater than 4 to 1.

* * * * *

UNITED STATES PATENT AND TRADEMARK OFFICE
CERTIFICATE OF CORRECTION

PATENT NO. : 5,434,047
DATED : July 18, 1995
INVENTOR(S) : Lyle J. Arnold, Jr.

It is certified that error appears in the above-identified patent and that said Letters Patent is hereby corrected as shown below:

Column 4, Line 66: after "described below." insert --PROBE/TARG; PROBE/M-TARG; M-PROBE/M. TARG and M-PROBE/TARG.--.

Column 4, Line 68: after "possible hybrids.", insert --The temperatures indicated are the melting temperatures of the match and mismatch hybrids in the first example--.

Column 7, Table 1, Section 1B: in the row starting with "Target", under columns "C", "D", "E" and "F", delete the number "1".

Column 11, Line 38: delete "1, 3 or 4" and insert --1, 2 or 3--.

Column 12, Line 58: delete "9, 10, 11 or 12" and insert --9, 10, 11 or 13--.

Signed and Sealed this

Twenty-seventh Day of October, 1998

Attest:

BRUCE LEHMAN

*Attesting Officer*  *Commissioner of Patents and Trademarks*